United States Patent [19]

Brown

[11] Patent Number: 4,933,165

[45] Date of Patent: Jun. 12, 1990

[54] COENZYME $Q_{10}$ WITH HMG-COA REDUCTASE INHIBITORS

[75] Inventor: Michael S. Brown, Dallas, Tex.

[73] Assignee: Merck & Co., Inc., Rahway, N.J.

[21] Appl. No.: 298,535

[22] Filed: Jan. 18, 1989

[51] Int. Cl.$^5$ .................. A61K 31/405; A61K 31/35; A61K 31/21; A61K 31/12

[52] U.S. Cl. ..................................... 424/10; 514/415; 514/460; 514/510; 514/689

[58] Field of Search .................. 424/10, 510; 514/415, 514/690, 460, 922, 689

[56] References Cited

PUBLICATIONS

The New England Journal of Medicine, Scott M. Grundy 319 No. 1, pp. 24–33 Jul. 7, 1988.

Folkers et al, Proc. Natl. Acad. Sci., 82, 901(1985).
Folkers et al, Proc. Natl. Acad. Sci., 82, 4513(1985).
M. S. Brown & J. Goldstein, J. Lipid Res., 21, 505 (1980).
H. Mabuchi et al, N.E.J. Med., 478 (1981).

*Primary Examiner*—Douglas W. Robinson
*Assistant Examiner*—Raymond J. Henley, III
*Attorney, Agent, or Firm*—Melvin Winokur; Joseph F. DiPrima

[57] ABSTRACT

A pharmaceutical composition and method of counteracting HMG-CoA reductase inhibitor-associated myopathy is disclosed. The method comprises the adjunct administration of an effective amount of a HMG-CoA reductase inhibitor and an effective amount of Coenzyme $Q_{10}$.

4 Claims, No Drawings

COENZYME Q$_{10}$ WITH HMG-COA REDUCTASE INHIBITORS

BACKGROUND OF THE INVENTION

Coenzyme Q$_{10}$ (2,3-dimethoxy-5-methyl-6-decaprenyl-1,4-benzoquinone) is a redox component in the respiratory chain and is found in all cells having mitochondria. It is thus an essential co-factor in the generation of metabolic energy and is particularly important in muscle function. For example, Folkers et al., Proc. Natl. Acad. Sci., 82: 901 (1985) have measured the levels of Coenzyme Q$_{10}$ (CoQ$_{10}$) in endomyocardial biopsy samples taken from patients with varying stages of cardiomyopathy. Folkers et al. states that these data show decreasing tissue levels of CoQ$_{10}$ with increasing severity of the symptoms of cardiac disease. Folkers et al., Proc. Natl. Acad. Sci., 82: 4513 (1985) in a double-blind study have reported improved cardiac output for some patients upon receiving an oral administration of CoQ$_{10}$.

HMG-CoA reductase inhibitors represent a new class of cholesterol-lowering drugs. Relatively low doses of these drugs effectively reduce plasma cholesterol levels. These drugs are believed to function by inhibiting the chemical transformation HMG-CoA to mevalonate, which is an early and rate-limiting step in the biosynthesis of cholesterol. A branch of the mevalonate cholesterol biosynthetic pathway in mammalian cells leads to the formation of CoQ$_{10}$. [reviewed by Brown and Goldstein J. Lipid Res., 21, 505 (1980)]. Furthermore high levels of lovastatin can reduce CoQ$_{10}$ in the liver (MK-803 NDA report) and compactin reduces LDL-bound CoQ$_{10}$ at doses employed in humans [H. Mabuchi et al, N. E. J. Med., 478 (August 1981].

The Physician's Desk Reference, 42d Ed., 1366 (1988) states that myalgia has been associated with lovastatin therapy. Tobert, N. E. J. Med., 48 (Jan. 7, 1988) states that in a very small number of patients (0.5 percent) myopathy appeared to be associated with lovastatin therapy. Concomitant therapy with immunosuppressant drugs, including cyclosporine, with gemfibrozil or niacin or a combination, appears to increase the risk of myopathy. (J. A. Tobert, Am. J. Cardiol. 1988, 62: 28J-34J). The myopathy is reversible upon discontinuance of lovastatin therapy.

Although cholesterol-lowering therapy through the use of HMG-CoA reductase inhibitors is generally free of side reactions, it would be of considerable benefit to counteract the myopathy observed in a small percent of patients. Since CoQ$_{10}$ is of benefit in congestive heart failure patients the combination with HMG-CoA reductase inhibitors should be of value in such patients who also have the added risk of high cholesterol levels.

DETAILED DESCRIPTION OF THE INVENTION

The present invention relates to a method of counteracting HMG-CoA reductase inhibitor-associated myopathy in a patient receiving HMG-CoA reductase therapy which comprises the adjunct administration of an effective amount of an HMG-CoA reductase inhibitor and an effective amount of Coenzyme Q$_{10}$. Included within the scope of the present invention is the treatment of those patients receiving HMG-CoA reductase therapy and who are also taking immunosuppressant drugs, gemfibrozil or niacin.

The HMG-CoA reductase inhibitor employed may be lovastatin, simvastatin, pravastatin, XU-62-320 (Sodium-3,5-dihydroxy-7-[3-(4-fluorophenyl)-1(methylethyl)-1H-Indole-2yl]-hept-6-enoate) or any other member of the class of compounds that inhibit HMG-CoA reductase. The preparation of lovastatin (U.S. Pat. No. 4,231,938), simvastatin (U.S. Pat. No. 4,444,784) and pravastatin (U.S. Pat. No. 4,346,227) have been described in the patent literature. The preparation of XU-62-320 is described in WIPO Pat. No. WO84/02131, published June 7, 1984. These methods of preparation are hereby incorporated by reference.

Coenzyme Q$_{10}$ is manufactured by the Kanegafuchi Chemical Industry Co., Ltd. and is widely available.

In its application to the counteraction of myopathy the present invention is accordingly to be understood as providing for the avoidance of myopathy where this may otherwise occur as well as the amelioration of myopathy. The term counteracting is accordingly to be understood as connecting both a precautionary or prophylactic as well as curvative or treatmental function.

In accordance with the method of the present invention, an HMG-CoA reductase inhibitor and CoQ$_{10}$ can be administered separately at different times during the course of therapy or concomitantly in divided or single combination forms. Thus treatment with CoQ$_{10}$ can commence prior to, subsequent to or concurrent with the commencement of HMG-CoA reductase treatment. The present invention is to be understood as embracing all such regimes of treatment and the term "adjunct administration" is to be interpreted accordingly.

The compounds of the instant invention may be administered orally or parenterally in the form of a capsule, a tablet, an injectable preparation or the like. The general amounts of HMG-CoA reductase inhibitor will be of the same or similar order to that employed in HMG-CoA reductase therapy. In general, satisfactory results are obtained by administration of 0.10 to 80 mg/day of the HMG-CoA reductase inhibitor in a single or divided dose. Doses of CoQ$_{10}$ may vary from 25 mg to 1 g day in a single or divided dose. Tablets or capsules may also be administered which contain both compounds in the dosage ranges indicated.

EXAMPLE 1

As a specific embodiment of a composition of this invention, 20 mg of lovastatin and 35 mg of Coenzyme Q$_{10}$ are formulated with sufficient finely-divided lactose to provide a total amount of 580 to 590 mg to fill a size 0 hard-gelatin capsule. Optionally added are a excipient such as finely divided cellulose, a disintegrant such as Explotat and a lubricant such as magnesium stearate.

What is claimed is:

1. A pharmaceutical composition comprising a pharmaceutical carrier and an effective antihypercholesterolemic amount of an HMG-CoA reductase inhibitor and an amount of Coenzyme Q$_{10}$ effective to counteract HMG-CoA reductase inhibitor-associated skeletal muscle myopathy.

2. A composition of claim 1 in which the HMG-CoA reductase inhibitor is selected from: lovastatin, simvastatin, pravastatin and sodium-3,5-dihydroxy-7-[3-(4-fluorophenyl)-1-(methylethyl)-1H-Indole-2yl]-hept-6-enoate.

3. A method of counteracting HMG-CoA reductase inhibitor-associated skeletal muscle myopathy in a subject in need of such treatment which comprises the adjunct administration of a therapeutically effective amount of an HMG-CoA reductase inhibitor and an effective amount of Coenzyme $Q_{10}$ to counteract said myopathy.

4. A method of claim 3 in which the HMG-CoA reductase inhibitor is selected from the group consisting of: lovastatin, simvastatin, pravastatin and sodium-3,5-dihydroxy-7-[3-(4-fluorophenyl)-1-(methylethyl)-1H-Indole-2yl]-hept-6-enoate.

* * * * *